(12) United States Patent
Staffler (10) Patent No.: US 6,623,630 B1
(45) Date of Patent: Sep. 23, 2003

(54) METHOD AND APPARATUS FOR MONITORING A FLUID SYSTEM

(75) Inventor: Michael Staffler, Fürstemfeldbruck (DE)

(73) Assignee: Dionex Corporation, Sunnyvale, CA (US)

(*) Notice: Subject to any disclaimer, the term of this patent is extended or adjusted under 35 U.S.C. 154(b) by 0 days.

(21) Appl. No.: 10/099,055

(22) Filed: Mar. 13, 2002

(51) Int. Cl.$^7$ .......................... B01D 17/12; B01D 15/08; G01F 1/56

(52) U.S. Cl. ..................... 210/87; 73/61.56; 73/861.08; 73/861.41; 210/198.2; 340/605; 340/609; 417/474

(58) Field of Search ............................... 95/82; 96/105; 20/85, 87, 198.2, 656, 739; 73/61.56, 861, 861.09, 861.41; 417/13, 474; 340/605, 606, 609; 422/70; 436/161

(56) References Cited

U.S. PATENT DOCUMENTS 5,254,976 A * 10/1993 Schueler .................. 340/605
6,019,897 A * 2/2000 Horsman et al. ........ 210/198.2
6,293,756 B1   9/2001  Andersson
6,299,767 B1  10/2001  Dourdeville

\* cited by examiner

*Primary Examiner*—Joseph Drodge
(74) *Attorney, Agent, or Firm*—Dorsey & Whitney LLP (57) ABSTRACT

An apparatus for monitoring a fluid system particularly suited for use with high pressure liquid chromatography systems. The apparatus monitors seal leakage as well as the general wellness of the apparatus and can thus be used to provide preventive maintenance feedback. The apparatus includes a liquid chamber, a wash chamber, a reservoir, a supply pump, a return line, and a detector. The liquid chamber includes a seal for sealing a fluid within the liquid chamber. The wash chamber is located adjacent the seal. The reservoir supplies a wash solution to the wash chamber. The supply pump supplies a unidirectional flow of wash solution from the reservoir to the wash chamber. The return line conveys a return flow from the wash chamber to the reservoir, in which the return flow includes any leakage of the fluid from the liquid chamber into the wash chamber and the portion of the wash solution that returns from the wash chamber to the reservoir. The detector determines whether there is a differential between the unidirectional flow and the return flow. A method of monitoring a fluid system is also disclosed.

19 Claims, 4 Drawing Sheets

METHOD AND APPARATUS FOR MONITORING A FLUID SYSTEM

BACKGROUND OF THE INVENTION

1. Field of the Invention

This invention relates to a new and improved method and apparatus for monitoring a fluid system, and is particularly suitable for use with high pressure liquid chromatography (HPLC) pumps having active rear seal washing.

2. Description of Related Art

High pressure liquid chromatography (HPLC) generally requires the components of a sample to be separated or analyzed be dissolved in a mobile phase liquid, termed an eluent, and conveyed by that liquid to a stationary phase, that is, a chromatography column. HPLC eluent delivery systems are used to supply the liquid and deliver the liquid, with dissolved sample, to the column. Selected pressures ranging from substantially atmospheric pressure to pressures on the order of ten thousand pounds per square inch are common to force the liquid into the column. Specially designed HPLC pumps are used to withstand extreme pressures and to deliver the liquid at precisely controlled flow rates in a smooth and uniform manner.

HPLC pumps are generally piston pumps with plungers formed of sapphire or ceramics. The pump heads include special high pressure seals that may have lips pressed against the plunger surface by the pressure built up in the pump head, that is, the system pressure. As the piston moves to aspirate new eluent, small amounts of eluent residing in the head chamber of the pump are commonly transported by the piston surface through the seal to the backside of the seal. This leaking amount is normally so small that it evaporates and does not disturb the pumping process.

Salt-containing eluents are commonly used, especially in biochemical applications. However, if the pumped eluent contains such salts, such evaporation may cause problems, because after a few pump strokes, salt crystals may build up on the backside of the seal. Such crystals are often sharp and can destroy the seal surface within a few piston strokes. In order to prevent the growth of salt crystals on the rear side of the seal it is common practice to keep the piston wet via a wash chamber filled with an aqueous wash solution, which is sometimes spiked with organic solvent. This organic addition to the wash solution prevents growth of algae and fungi inside the wash chamber.

Such wash chambers must be maintained as the wash solution becomes contaminated by the pumped eluent leaking through the seal. If not regularly replaced, the wash solution can become very salty and so precipitate which could destroy the sealing. Conventionally, wash solution within the wash chamber is replaced using a manual syringe fluidly connected to the wash chamber. Disadvantageously, washing by a hand syringe requires the operator to remember to replace the wash solution on a regular basis. Typically, wash solution replacement is done in a haphazard manner and the seal wears out prematurely.

Some advanced wash designs include a small auxiliary pump which transports fresh wash solution into and through the wash chambers at regular time intervals. Such advanced designs are sometimes referred to as active back seal washing. The wash solution replacement cycle depends on the salt load and the pressure at which the HPLC pump is run. As biochemical applications are increasingly common, salt-containing eluents are more popular than ever. As a consequence, such active seal washing is becoming increasingly popular.

Another increasingly popular concept is wellness, that is, preventive maintenance monitoring. Preventive maintenance monitoring is highly desirable in HPLC systems as uptime is an overwhelming criterion of HPLC systems. In many cases downtime implies lost samples, which in the pharmaceutical industry can be very costly. Furthermore, if production quality control is down in the pharmaceutical industry, drug production would be blocked immediately. Thus, preventive maintenance monitoring of HPLC systems is highly desirable because HPLC is the standard method used in pharmaceutical production quality control.

HPLC pumps contain several wear parts, which must be replaced periodically. The most stressed wear part in a HPLC pump is the high pressure seal. As a HPLC pump contains at least two pistons, there are two seals which must be regularly replaced. Such seals are expected to survive millions of piston strokes at high friction. Undetected seal wear is by far the most frequent reason for unexpected pump downtime. Furthermore, undetected seal wear may impair the quality of the analysis, and even permanently damage other expensive parts of the HPLC pump. For example, the wash solution can eventually run into the ball bearings of a piston pusher and cause the destruction thereof.

What is needed is a leakage monitoring for a system including a high pressure seal which overcomes the above and other disadvantages of known systems including a high pressure seal.

SUMMARY OF THE INVENTION

In summary, one aspect of the present invention is directed to an apparatus including a liquid chamber, a wash chamber, a reservoir, a supply pump, a return line, and a detector. The liquid chamber includes a seal for sealing a liquid within the liquid chamber. The wash chamber is located adjacent the seal. The reservoir supplies a wash solution to the wash chamber. The supply pump supplies a unidirectional flow of wash solution from the reservoir to the wash chamber. The return line conveys a return flow from the wash chamber to the reservoir, in which the return flow includes any leakage of the liquid from the liquid chamber into the wash chamber and the portion of the wash solution that returns from the wash chamber to the reservoir. The detector determines whether there is a differential between the unidirectional flow and the return flow.

In one embodiment, the liquid chamber is a pump chamber of a high pressure liquid chromatography (HPLC) pump. The HPLC pump may include a piston extending through the pump chamber, the seal, and the wash chamber. The apparatus may include one, two, three or more liquid chambers and corresponding one, two, three or more wash chambers, in which each of the liquid chambers includes a seal, and each of the wash chambers is adjacent a respective one of the seals.

Preferably, the supply pump is a peristaltic pump. Preferably, the detector is a drop counter. In one embodiment, the detector includes a cap releasably engaging the reservoir, a return passageway for fluid connection with the return line, the return passageway extending through the cap, and a pair of spaced electrodes extending through the cap and into the reservoir, the ends of the electrodes are positioned below the return passageway such that a drop of wash solution falling from the return passageway into the reservoir bridges a space between the ends as the drop passes the ends.

The apparatus may include a detection circuit, to which the electrodes are operably coupled for monitoring the number of drops of wash solution that pass between and bridge the space between the electrodes. The detection circuit may monitor the operational state of the supply pump. The detection circuit may provide a first signal indicating that the supply pump is running and the detector senses drops of return flow entering the reservoir. The detection circuit may provide a second signal indicating that the supply pump is running and the detector does not sense drops of return flow entering the reservoir. The detection circuit may provide a third signal indicating that the supply pump is not running and the detector senses drops of return flow entering to the reservoir. The detection circuit may provide a fourth signal indicating continuous conductivity between the electrodes.

Another aspect of the present invention is directed to a method of monitoring leakage in a system including a liquid chamber, a seal for sealing a liquid under within the liquid chamber, and a wash chamber adjacent the seal. The method includes the steps providing a unidirectional flow of a wash solution from a reservoir to the wash chamber and determining whether there is a differential between a return flow and the unidirectional flow, the return flow including any leakage of the liquid from the liquid chamber into the wash chamber and the portion of the wash solution that returns from the wash chamber to the reservoir.

The method may include the step of providing a first signal indicating that the return flow is above a predetermined threshold based upon the unidirectional flow. The method may include the step of providing a second signal indicating that the unidirectional flow is greater than the return flow. The method may include the step of providing a third signal indicating that the unidirectional flow is less than the return flow. The method may include the step of providing a fourth signal indicating that the level of the reservoir exceeds a predetermined level.

An object of the present invention is to provide a method and apparatus for monitoring a fluid system.

Another object of the present invention is to provide a method and apparatus of the above character for use with a high pressure liquid chromatography (HPLC) pump having an active rear seal washing system.

Yet another object of the present invention is to provide a method and apparatus of the above character suitable for continuous leak monitoring for determining a state of seal degradation.

It is a further object of the present invention to provide a method and apparatus of the above character for monitoring the operational state, or wellness, of the active rear seal washing system.

The method and apparatus for monitoring high pressure a fluid system in accordance with the present invention has other features and advantages which will be apparent from or are set forth in more detail in the accompanying drawings, which are incorporated in and form a part of this specification, and the following Detailed Description of the Invention, which together serve to explain the principles of the present invention.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

High pressure liquid chromatography (HPLC) pumps are specially designed to withstand high pressure and to deliver liquids at precisely controlled flow rates in a smooth and uniform manner. For the purposes discussed herein, the term "high pressure" refers to the operational pressure of HPLC pumps which may range from approximately atmospheric pressure to pressures on the order of ten thousand pounds per square inch.

One should appreciate that seal leakage of an HPLC pump leads to flow inaccuracy. With new seals, such inaccuracy is generally below 0.05% at approximately 300 bars and substantially less if the HPLC pumps are run at more conventional pressures of approximately 100 bars. The level of leakage depends upon various factors including type of pump used such as a low pressure gradient (LPG) pump, a high pressure gradient (HPG) pump, or an HPG-prep pump. Other factors upon which the level of leakage also depends include the particular eluent used and, especially, the viscosity of that eluent, the flow rate, and the system pressure, that is, operating pressure of the pump.

Such pump leakage is known as chromatographers and technicians often observe that salt crystals commonly build up on the backside of the high pressure seals of HPLC pumps. Users of conventional HPLC pumps often observe that a back seal washing pipeline of such pumps fills up after a while. Astute users would recognize that such observation signifies that leakage through the high pressure seals has occurred. However, if users are inattentive or do not recognize the significance of their observation, serious damage may occur to the HPLC pump.

The apparatus for monitoring a fluid system of the present invention continuously monitors an active rear seal washing system of an HPLC pump in order to determine whether leakage through the high pressure seals of the HPLC pump has occurred. The apparatus for monitoring a fluid system of the present invention also monitors the general operational status the active rear seal washing system, also referred to as a wash solution circuit. In particular, the apparatus of the present invention can be used to positively alert a technician of leakage through the high pressure seals of the HPLC pump, the degree of such leakage, and also the general operational status of the active rear seal washing circuit, also referred to as a wash solution system. One should appreciate, however, that the method and apparatus of the present invention is also suitable for use in monitoring other types of pumps and/or fluid systems for monitoring seal leakage of the pump and/or fluid systems.

Figure 1:
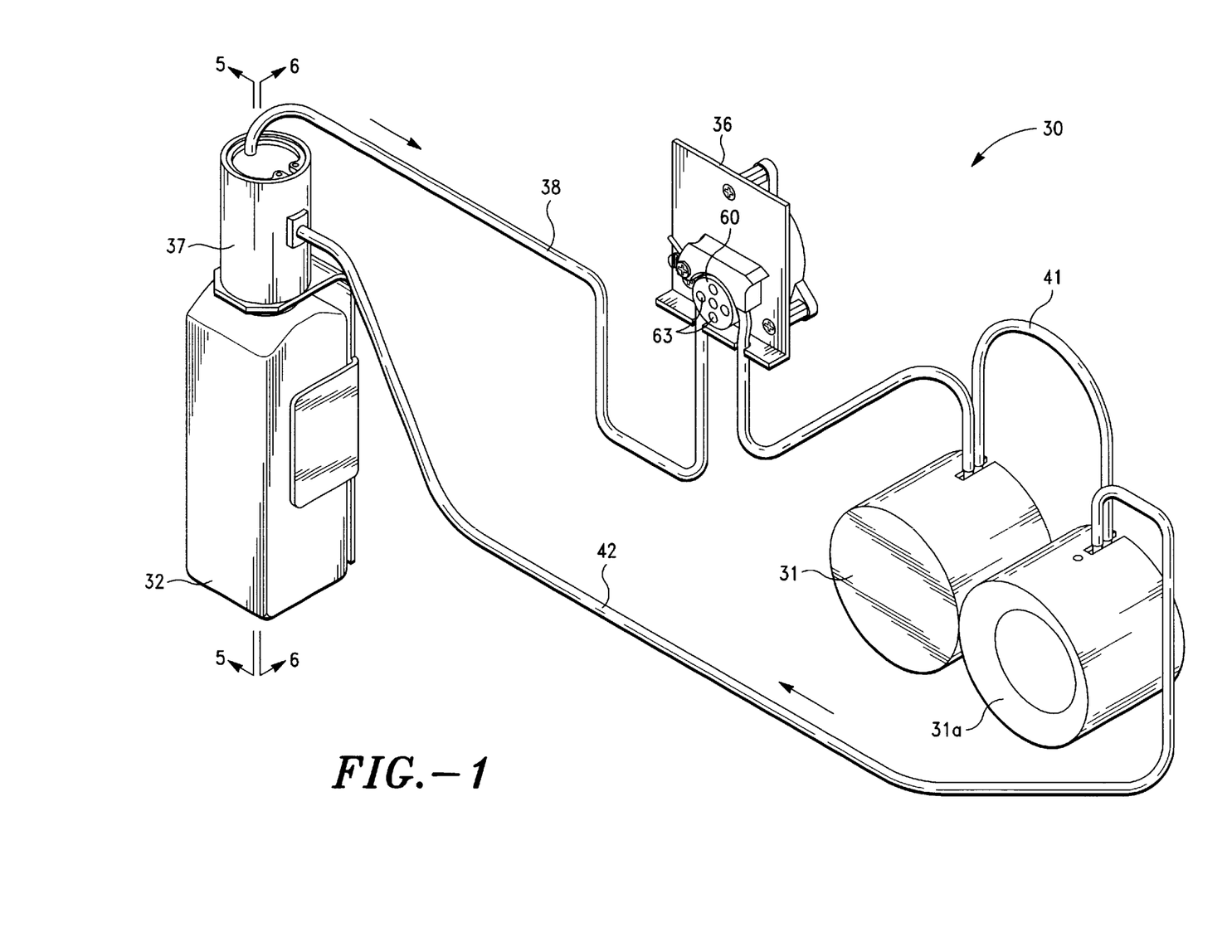
FIG. 1 is a perspective view of an apparatus for monitoring a fluid system in accordance with the present invention.

Turning now to the drawings, wherein like components are designated by like reference numerals throughout the various figures, attention is directed to FIG. 1 which shows an apparatus 30 for monitoring a fluid system in accordance with the present invention. Apparatus 30 is particularly useful in monitoring the high pressure seals of an HPLC pump. Apparatus 30 generally includes a rear seal washing circuit, which is a generally closed circuit, that extends from a wash solution reservoir 32, to a peristaltic pump 36, through one or more HPLC pumps, e.g., 31, 31a, and returns to the reservoir through a flow detector 37. In particular, the closed fluid circuit includes a supply line 38 extending to a first HPLC pump 31, an intermediate line 41 extending from the first HPLC pump to a second HPLC pump 31a, and a return line 42 extending from the second HPLC pump to detector 37.

Figure 2:
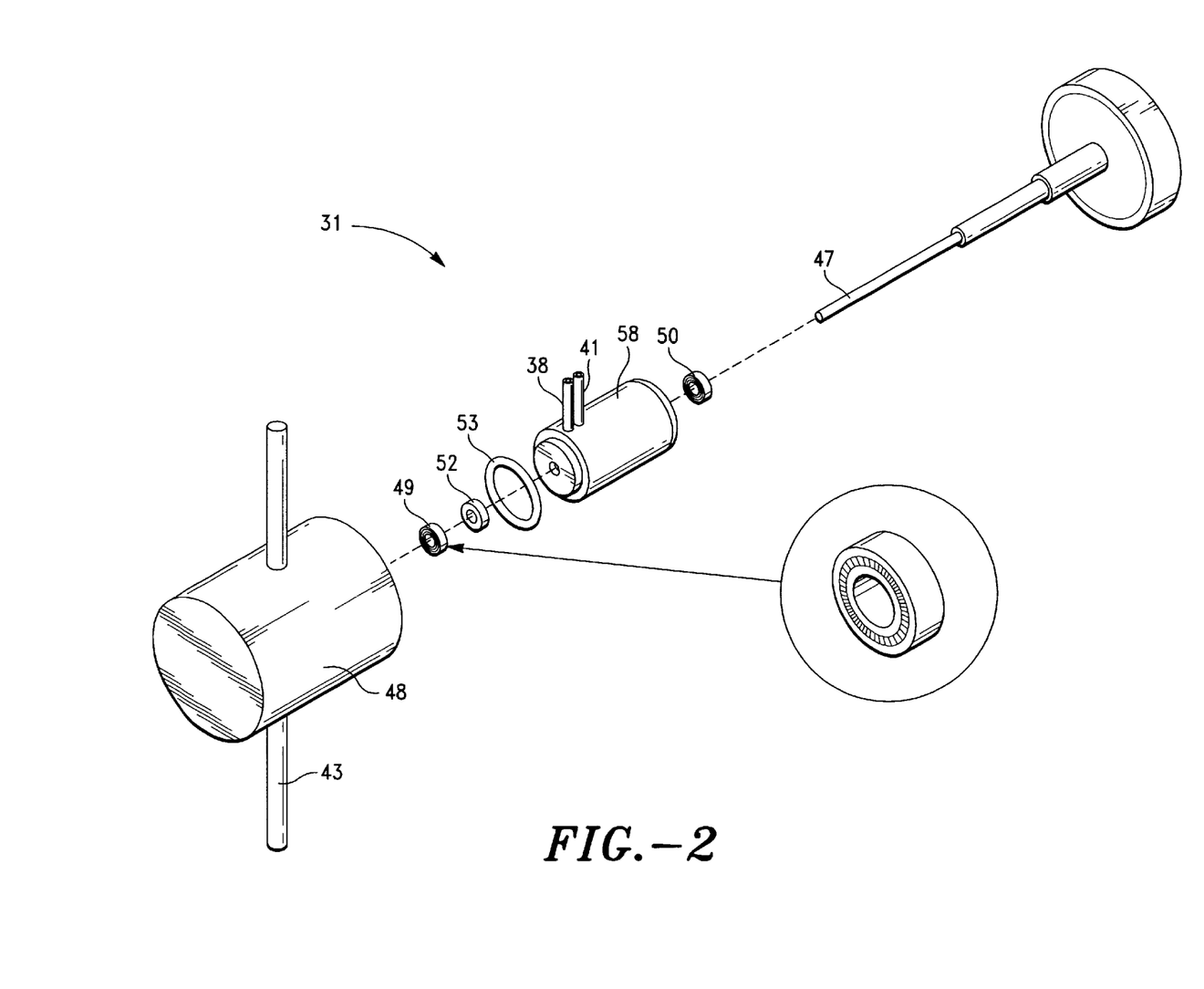
FIG. 2 is an exploded perspective view of an HPLC pump with which the apparatus of FIG. 1 is used, the view including an enlarged detailed view of a high pressure seal.

In one embodiment shown in FIG. 2, HPLC pump 31 is a piston pump that pumps chromatography eluent along an eluent supply line 43 forming a mobile phase to be delivered to a chromatography column in a well known manner. HPLC pump 31 includes a reciprocating plunger or piston 47 which operably extends into a high pressure chamber or head chamber formed within a housing 48 of HPLC pump 31. Piston 47 is formed of sapphire, zirconium, ceramics or other known suitable materials. High pressure chamber 48 is fluidly sealed, in part, by one or more high pressure seals 49, 50 through which plunger 47 extends.

As shown in FIG. 2, a rear side of high pressure seal 49 is followed by a small support ring 52 and a seal ring 53. As piston 47 moves backward, that is, toward the right in FIG. 2, to aspirate new chromatography eluent, small amounts of the chromatography eluent residing in head chamber 48 are transported by the surface of piston 47 through high pressure seal 49 to the backside of seal 49, that is, the right side. Even when high pressure seal 49 is new, such leakage of chromatography eluent may occur in trace amounts. In fact, such leakage is within conventional manufacturing specifications which allow for flow accuracies of 0.1% to 1% at 1 ml/min. Generally, such leakage is insignificant and the trace amounts of eluent merely evaporate and do not disturb the pumping process.

If the pumped chromatography eluent contains salt additions, however, such leakage and subsequent evaporation is undesirable because small salt crystals may build up on the back side of high pressure seal 49 after but a few pump strokes or cycles. These salt crystals can be quite sharp and can destroy seal 49 within a few piston strokes.

A wash chamber 58 is provided to minimize and/or prevent the growth of salt crystals on the rear side of high pressure seal 49 due to the leakage of chromatography eluent through seal 49. As most clearly shown in FIG. 4, wash chamber 58 includes a bore 57 through which plunger 47 extends. A ring gap is formed between the surface of piston 47 and the surface of bore 57 of wash chamber Known HPLC pumps may have a ring gap on the order of approximately 0.2 mm. Any chromatography eluent leaking through high pressure seal 49 will be forced through the ring gap between piston 47 and bore 57 into wash chamber 58. Thus, such leaking chromatography eluent may also contact the backside of seal 49 leading to the degradation of seal 49. In fact, such leakage may seep to and contact other components of the system causing permnanent and expensive damage to such components.

Figures 3, 4:
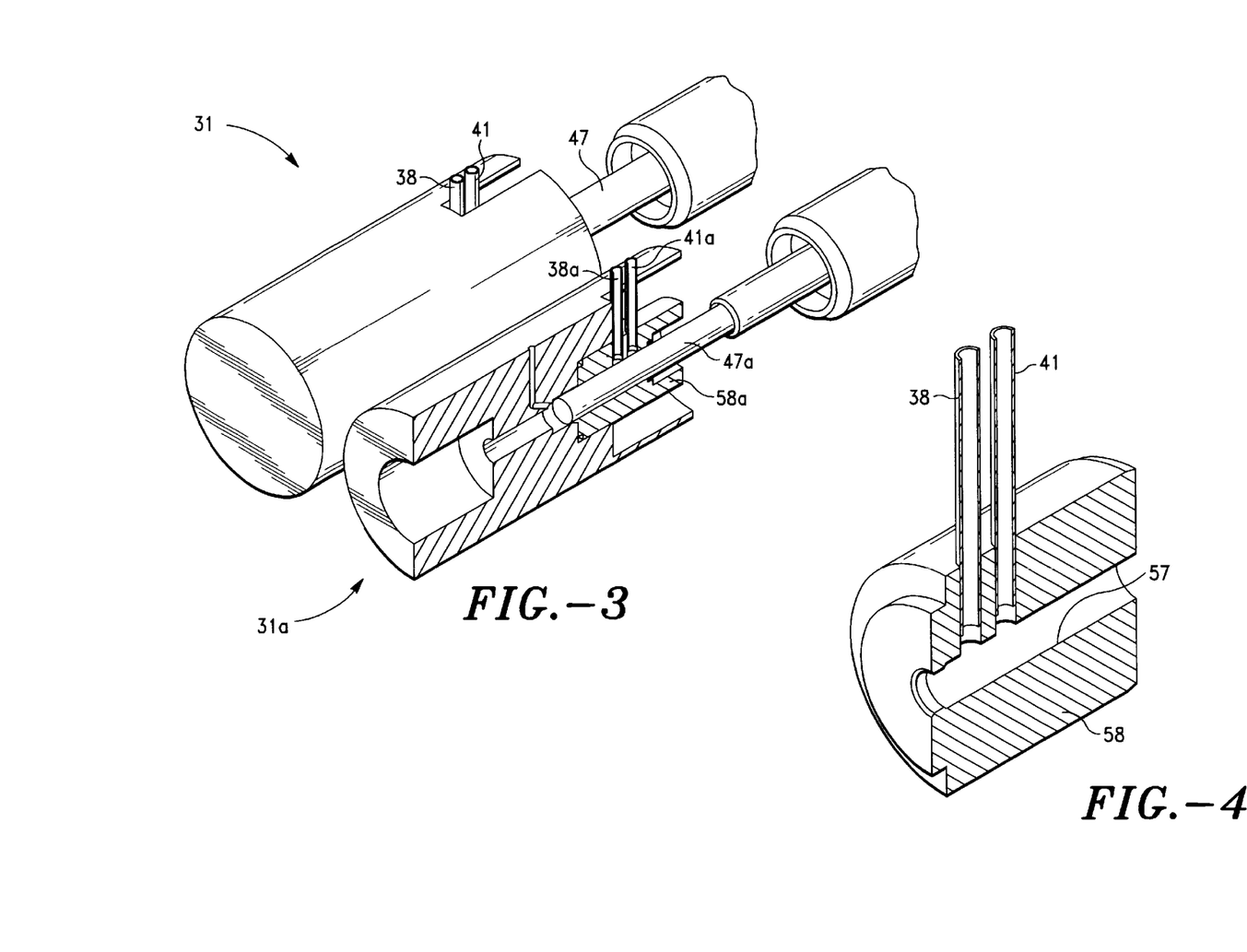
FIG. 3 is a partially cross-sectional exploded perspective view of two HPLC pumps with which the apparatus of FIG. 1 is used, each pump including a wash chamber.
FIG. 4 is an enlarged partially cross-sectional view of one wash chamber of FIG. 3.

In order to inhibit and/or prevent the deleterious effects of such leakage, wash chamber 58 is designed to deliver a wash solution to the surface of piston 47 in order to keep piston 47 wet and thus prevent the formation of salt crystals. The wash solution is generally water, however, one should appreciate that other wash solutions can be used. Preferably, the wash solution is water which is spiked with approximately 5% to 10% organics to prevent the growth of algae and fungi within the wash chamber. For example, one wash solution that can be used in accordance with the present invention is water containing approximately five percent MeOH.

The wash solution is delivered to wash chamber 58 via supply line 38. The wash solution thus enters wash chamber 58 and circumvents the portion of piston 47 which extends though wash chamber 58. The backside of wash chamber 58 is sealed by a second seal 50. The wash solution exits wash chamber 58 via intermediate line 41 and thus flushes out some or all of the chromatography eluent present within wash chamber 58 due to leakage.

As shown in FIG. 1, peristaltic pump 36 is utilized to pump the wash solution toward and into wash chamber 58 within HPLC pump 31. In particular, peristaltic pump 36 aspirates wash solution through wash solution supply line 38 and pushes the wash solution through the high pressure chambers within HPLC pumps 31 and 31a. Peristaltic pump 36 includes a large diameter wheel 60 carrying small diameter rollers 63 which squeeze supply line tubing 38 thus pushing wash solution along wash solution supply line 38 and through an inlet into wash chamber 58 of HPLC pump 31.

Peristaltic pump 36 is particularly suited for use with the present invention because it is of a simple conventional design and does not come in contact with the wash solution. Thus, the peristaltic pump is not subject to corrosion due to the wash solution. The simple mechanical design of peristaltic pump 36 prevents backflow of wash solution within wash solution supply line 38 when peristaltic pump 36 is stopped. This configuration of peristaltic pump 36 provides a unidirectional configuration, the advantages of which will become apparent below. One should appreciate that the unidirectional flow of wash solvent through supply line can be approximated in a well known manner based upon several factors including, but not limited to, the peristaltic pump speed and the diameter of the supply line.

When apparatus 30 is functioning properly, that is, when wash solution is not leaking out of the washing solution circuit and an excessive amount of eluent is not leaking into the washing solution circuit, the return flow is substantially equal to the unidirectional flow. One should appreciate that the flow of wash solution is typically a magnitude of two to three times greater than the flow of eluent through an HPLC pump. Thus, when eluent leakages are within manufacturing specifications of HPLC pumps, the return flow will be within a fraction of one percent of the unidirectional flow. Accordingly, an expected return flow back to the reservoir may be determined based upon the approximated unidirectional flow rate set by the peristaltic pump. A predetermined expected threshold may be set at a desired percentage of the expected return flow for the purpose of determining whether apparatus 30 is fuinctioning properly.

One should appreciate that other types of pumps may be used in accordance with the invention instead of a peristaltic pump. For example, a piston pump equipped with a check valve would also provide a simple unidirectional configuration for supplying wash solution in accordance with the present invention.

Alternatively, a membrane pump mechanism derived from the main piston movement combined with a check valve, a unidirectional membrane pump driven by a motor, or other suitable configurations can be used in accordance with the present invention.

In the embodiment shown in FIG. 1, intermediate line 41 fluidly connects an outlet of wash chamber 58 of HPLC pump 31 to an inlet of wash chamber 58a of HPLC pump 31a. As noted above, one, two, three or more pumps and a corresponding number of wash chambers may be utilized in accordance with the present invention. Accordingly, an appropriate number of intermediate lines will be provided that fluidly connect the wash chambers with one another. Return line 42 extends from an outlet of wash chamber 58a and feeds the wash solution back into reservoir 32 through detector 37.

Figure 5:
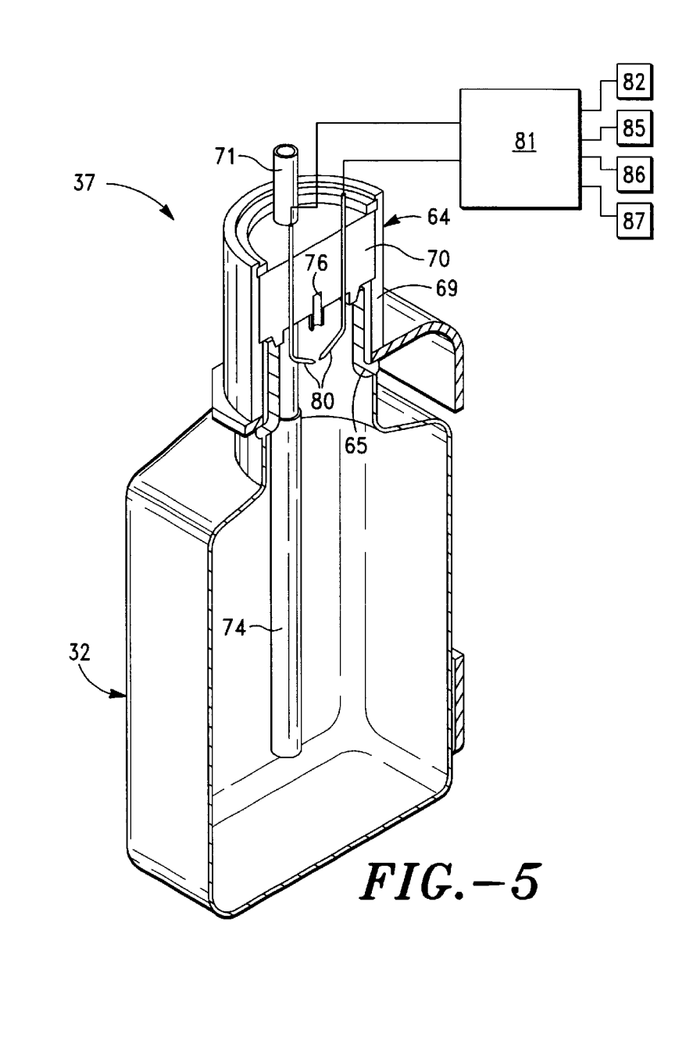
FIG. 5 is cross-sectional perspective view of a reservoir and detector of the apparatus of FIG. 1 taken along line 5—5 of FIG. 1.
Figure 6:
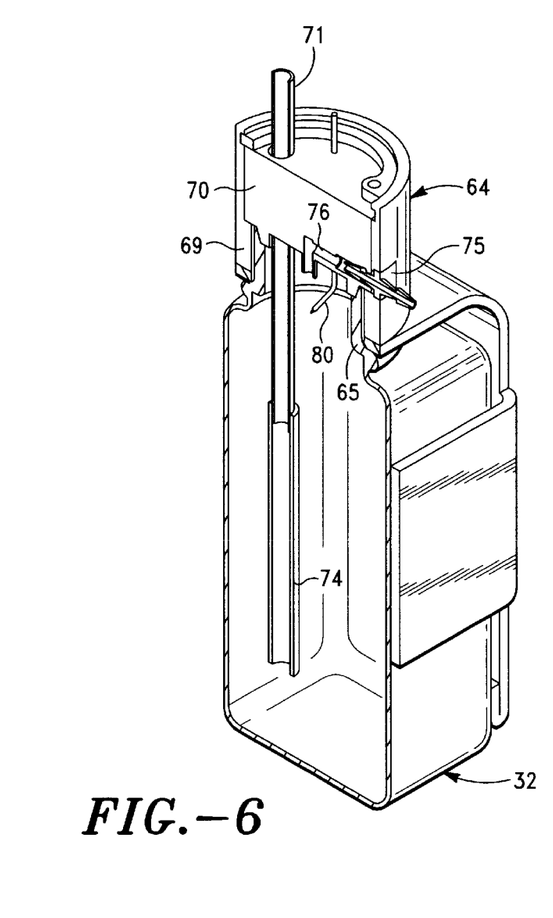
FIG. 6 is cross-sectional perspective view of a reservoir and detector of the apparatus of FIG. 1 taken along line 6—6 of FIG. 1.

In one embodiment shown in FIGS. 5 and 6, flow detector 37 is integrally formed with a reservoir cap 64 for reservoir 32. Reservoir 64 cap engages neck 65 of reservoir 37 and fluidly seals the reservoir in a well known manner. Reservoir cap 64 includes a cylindrical skirt 69 and a removable base 70 received within skirt 69. In the illustrated embodiment, base 70 is secured to skirt 69 by a spring clip in a well known manner. One should appreciate, however, that base 70 and skirt 69 can be integrally formed in accordance with the present invention.

Base 70 includes a supply outlet 71 to which supply line 38 is removably attached. Base 70 supports a feed line 74 which extends downward adjacent the bottom of reservoir 32. Base 70 also includes a return port 75 which receives return line 42 and fluidly communicates with a return passageway 76 through which wash solution from return line 42 returns to reservoir 32.

Reservoir cap 64 is provided with a conductivity detector in the form of a drop counter. A pair of diametrically opposed pins 80 extend downwardly from base 70 and into the interior of reservoir 32. Pins 80 form the electrodes of an electronic detector circuit 81 for determining the number of drops of wash solution which fall between pins 80 as wash solution returns to reservoir 32. Preferably, the pins are formed of or plated with a conductive material. For example, the electrodes may be formed of copper, gold, platinum, silver, titanium, or other suitable metal in accordance with the present invention.

The ends of pins 80 are arranged such that drops of wash solution falling from return passage 76 momentarily contact the ends of both pins 80. As the wash solution has some degree of conductivity, when each drop thereof momentarily contacts both pins 80, each drop also momentarily closes the circuit of detector circuit 81. Thus, enabling detector circuit 81 can determine the number of drops which pass between pins 80 and thus the flow of wash solution returning to reservoir 32. In particular, detector circuit 81 determines the number of drops passing between pins 80 per unit of time and thus can determine the flow rate of wash solution returning to reservoir 32.

As the unidirectional flow of wash solution through supply line 38 can be approximated by well known means, and the detector circuit 81 can determine the return flow rate of wash solution returning to reservoir 32, flow detector 37 can determine whether there is a differential between the unidirectional flow and the return flow. The term "differential" can refer the actual difference in flow rates between the unidirectional flow and the return flow. For the purposes of the present invention, however, the term "differential" also applies to the following circumstances: flow detector 37 does not detect a return flow even though peristaltic pump 36 is running and it is assumed that a unidirectional flow exists; and flow detector 37 detects a return flow even though peristaltic pump 36 is not running and it is assumed that a unidirectional flow does not exist.

Pins 80 also extend into the reservoir below a predetermined fluid height such that the electronic circuit is also bridged when wash solution in the reservoir exceeds the predetermined height or level. This configuration of pins 80 further allows the detector circuit 81 to determine the fullness of the reservoir. For example, if detector circuit 81 detects constant conductivity between pins 80, detector circuit issues a signal indicating that the reservoir is full.

Generally, the flow of wash solution returning along return line 42 generally forms drops at the bottom edge of return passage 76 which fall back into reservoir 32. Although fluid drop sizes varies depending upon the composition thereof, the drop sizes of a particular fluid are fairly consistent.

Although the illustrated embodiments provides a relatively simple and reliable apparatus for monitoring a fluid system, one should appreciate that other methods of monitoring a fluid system can be used in accordance with the present invention. For example, an apparatus in accordance with the present invention can monitor the combined weight of the reservoir and the fluid therein to determine whether leakage is causing the return flow to the reservoir that is greater than the supply flow of wash solution. Similarly, an apparatus can monitor the liquid surface height of fluid within the reservoir to determine whether leakage is causing the return flow to the reservoir that is greater than the supply flow of wash solution thus increasing the volume of fluid in the reservoir. For example, an optical sensor or a swimmer can be used to monitor the liquid surface height. Furthermore, a flow meter can be installed in the return line to determine whether leakage is causing the return flow to the reservoir that is greater than the supply flow of wash solution.

One should also appreciate that the actual detection of drops can vary in accordance with the method and apparatus of the present invention. For example, an optical drop detection sensor such as a light barrier can be used to detect drops falling into the reservoir. Alternatively, a capacitive drop detection sensor can be used to detect drops falling into the reservoir.

In operation and use, the illustrated system 30 monitors the return flow rate of wash solution returning to reservoir 32 in combination with the operational status, that is, a parameter of peristaltic pump 36 and allows a technician to distinguish several operational conditions.

Firstly, if peristaltic pump 36 is running and flow detector 37 senses drops, detector circuit 81 produces a first signal 82 indicating that reservoir 32 carries enough wash solution to wash circulate through wash chamber 58 and wash the back side of high pressure seal 49. This first operational state is generally activated periodically in order to rinse any leakage from the surface of piston 47 and from the backside of high pressure seal 49. As the active rear seal washing circuit or wash solution system operates approximately 5 minutes for every operational hour of an HPLC pump, this first operational state generally has an approximate 8% duty cycle.

As noted above, when apparatus 30 is functioning properly, the return flow is substantially equal to the unidirectional flow. Thus, detector circuit may be provided to produce first signal 82 when flow detector 37 senses a return flow that exceeds a predetermined expected threshold thus signifying that apparatus 30 is functioning properly.

Secondly, in the event peristaltic pump 36 is running, but flow detector 37 senses no drops returning to reservoir 37, detector circuit 81 produces a second signal 85 indicating that a component of the apparatus has failed. This second operational state indicates that either the reservoir is empty or that the closed wash solution circuit has failed. For example, one of lines 38, 41 and 42 is leaking causing the wash solution is leaking therefrom instead of returning to reservoir 32. Accordingly, when apparatus 30 determines that the second operational state exists, the system issues second signal 85 as an appropriate warning signal.

Thirdly, if peristaltic pump 37, is not running, but flow detector senses drops returning to reservoir 37, detector circuit 81 produces a third signal 86 indicating that one of the high pressure seals, for example, seal 49 is leaking. Due to the configuration of peristaltic pump 37, peristaltic pump 37 pinches off or closes supply line 38 when the pump is stopped. As the wash solution circuit is a closed circuit, wash solution cannot backflow and return to reservoir via supply line 38 continue downstream and return to the reservoir via return line 42 once peristaltic pump 37 is stopped. This third operational state indicates that an HPLC pump is pumping chromatography eluent through the wash solution circuit. Accordingly, when apparatus 30 determines that the third operational state exists, the system issues third signal 86 as an appropriate warning signal.

Monitoring the third operational state is especially beneficial, because flow detector 37 can not only distinguish between "leak" and "no leak" conditions, but detector circuit also allows continuous monitoring of seal degradation. As noted above, the duty cycle of peristaltic pump 37 is low as it only runs for approximately 5 minutes per hour. During the remaining time, that is, during approximately 55 minutes flow detector 37 can count drops which are generated by leakage of the chromatography eluent through high pressure seal 49. While the seals are new or in acceptable condition, flow detector 37 will sense very few drops per hour. However, as the seals wear, flow detector 37 will sense an increasing number of drops while the pump is stopped. Thus, detection circuit 81 can be configured such that it can provide the third signal as a warning level based upon a predetermined "accepted drops per hour" threshold. Preferably, this warning threshold is adjustable.

Fourthly, if detection circuit 81 senses continuous conductivity, detection circuit 81 indicates that reservoir 32 is full and should be emptied. Generally, wash reservoir 32 is initially half filled with a wash solution such as water. Over time, reservoir 32 fills up due to leakage of seal 49. The worse the leakage is, the faster reservoir 32 fills. This fourth operational state indicates that the level of fluid within reservoir 32 has risen above the lower ends of pins 80 and thus continuously bridges the gap in the electronic circuit. Accordingly, when detection circuit 81 of apparatus 30 determines that the fourth operational state exists, the system issues a fourth signal 87 as an appropriate warning signal.

Although the apparatus of the illustrated embodiments are not configured to particularly pinpoint which one of several high pressure seals within an HPLC pump is leaking, the apparatus nonetheless alerts a technician that leakage has become an issue in which case all high pressure seals within the HPLC pump can be replaced with new ones. Although replacing all high pressure seals is slightly more expensive than replacing individual seals, it may be desirable to replace all high pressure seals in most cases in order to minimize chromatography system downtime.

Whether one, two, or all high pressure seals are replaced, a technician must temporarily decommission the HPLC pump. Thus the whole system is out of service for a predetermined period, often at least one day. The cost of such downtime far exceeds the relatively minute cost of replacing all seals. Moreover, if one seal has worn out, probability is high that the others will soon wear out. Alternatively, the technician can visually inspect the seals or isolate the seals while the pump is down in order to determine which high pressure seals must be replaced. In any event, the apparatus of the present invention is beneficial to regulated laboratories because the apparatus alerts a technician to leakage and, as leakage leads to inaccurate flow, immediate action may be taken.

Advantageously, the method and apparatus for monitoring a fluid system of the present invention can be used to continuously monitor pump density of the wash solution and thus continuously monitor high pressure seal.

Advantageously, the method and apparatus for monitoring a fluid system of the present invention provides feedback which can be used to monitor the wellness of system itself. In particular, a general warning based upon the feedback of the system can draw a technician's attention to the system and alert the technician that the peristaltic pump and/or the closed fluid circuit is not functioning properly.

An advantage of the method and apparatus for monitoring a fluid system of the present invention is that it provides reliable information which can be used to determine whether the reservoir requires attention either because it is above or below a predetermined threshold. For example, the apparatus can alert a technician that the reservoir is either full or empty.

Another advantage of the method and apparatus for monitoring a fluid system of the present invention is that it is a simple design which is inexpensive to fabricate and maintain.

Advantageously, the method and apparatus of the present invention allows leak monitoring which can be used to determine why a chromatographers's data peaks "wander out".

For convenience in explanation and accurate definition in the appended claims, the terms "up" or "upper", "down" or "lower", "inside" and "outside" are used to describe features of-the present invention with reference to the positions of such features as displayed in the figures.

In many respects the modifications of the various figures resemble those of preceding modifications and the same reference numerals followed by subscript a designate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An apparatus for monitoring a fluid system comprising:
   a liquid chamber;
   a seal for sealing a fluid within said liquid chamber;
   a wash chamber adjacent said seal on the opposite side of said seal from said liquid chamber;
   a reservoir for supplying a wash solution to said wash chamber;
   a supply pump for supplying a unidirectional flow of wash solution from said reservoir to said wash chamber;
   a return line for conveying a return flow from said wash chamber to said reservoir, said return flow including any leakage of said fluid from said liquid chamber into said wash chamber and the portion of said wash solution that returns to said reservoir; and
   a detector for determining whether there is a differential between said unidirectional flow and said return flow.

2. The apparatus of claim 1 wherein said liquid chamber is a pump chamber of a high pressure liquid chromatography (HPLC) pump.

3. The apparatus of claim 2 wherein said HPLC pump includes a piston extending through said pump chamber, said seal, and said wash chamber.

4. The apparatus of claim 1 further comprising a plurality of liquid chambers and a plurality of wash chambers, each said liquid chamber including a seal, and each said wash chamber being adjacent a respective one of said seals.

5. The apparatus of claim 1 wherein said supply pump is a peristaltic pump.

6. The apparatus of claim 1 wherein said detector comprises a drop counter.

7. The apparatus of claim 6 wherein said detector comprises a pair of spaced electrodes extending into said reservoir, the ends of said electrodes positioned such that a drop of wash solution falling into said reservoir bridges a space between said ends as the drop passes said ends.

8. The apparatus of claim 7 further comprising a detection circuit, said electrodes operably coupled with said detection circuit for monitoring the number of drops of wash solution that pass between and bridge the space between said electrodes.

9. The apparatus of claim 8 wherein said detection circuit monitors a parameter of said supply pump.

10. The apparatus of claim 9 wherein said detection circuit provides a first signal indicating that said supply pump is running and said detector senses drops of return flow entering said reservoir.

11. The apparatus of claim 9 wherein said detection circuit provides a second signal indicating that said supply pump is running and said detector does not sense drops of return flow entering said reservoir.

12. The apparatus of claim 9 wherein said detection circuit provides a third signal indicating that said supply pump is not running and said detector senses drops of return flow entering to said reservoir.

13. The apparatus of claim 8 wherein said detection circuit provides a fourth signal indicating continuous conductivity between said electrodes.

14. The apparatus of claim 7 further comprising a cap releasably engaging said reservoir and a return passageway for fluid connection with said return line, said return passageway extending through said cap, wherein said pair of spaced electrodes extend through said cap and into said reservoir, the ends of said electrodes positioned below said return passageway such that a drop of wash solution falling from said return passageway into said reservoir bridges a space between said ends as the drop passes said ends.

15. A method of monitoring leakage in a system including a liquid chamber, a seal for sealing a fluid under within said liquid chamber, and a wash chamber adjacent said seal, said method comprising the steps of:
   providing a unidirectional flow of a wash solution from a reservoir to said wash chamber;
   determining whether there is a differential between a return flow and said unidirectional flow, said return flow including any leakage of said fluid from said liquid chamber into said wash chamber and the portion of said wash solution that returns to said reservoir.

16. The method of claim 15 further comprising the step of providing a first signal indicating said return flow is above a predetermined expected threshold.

17. The method of claim 15 further comprising the step of providing a second signal indicating that said unidirectional flow is greater than said return flow.

18. The method of claim 15 further comprising the step of providing a third signal indicating that said unidirectional flow is less than said return flow.

19. The method of claim 15 further comprising the step of providing a fourth signal indicating that the level of said reservoir exceeds a predetermined level.

\* \* \* \* \*

UNITED STATES PATENT AND TRADEMARK OFFICE
CERTIFICATE OF CORRECTION

PATENT NO.    : 6,623,630 B1
DATED         : September 23, 2003
INVENTOR(S)   : Michael Staffler It is certified that error appears in the above-identified patent and that said Letters Patent is hereby corrected as shown below:

Column 12,
Line 23, change "fluid under within said" to -- fluid within said --

Signed and Sealed this

Eleventh Day of November, 2003

JAMES E. ROGAN
*Director of the United States Patent and Trademark Office*